United States Patent [19]

Druckrey et al.

[11] 4,024,274
[45] May 17, 1977

[54] BENZYLAMINE DERIVATIVES AND PROCESS FOR PREPARING THEM

[75] Inventors: Eike Druckrey, Rossert; Bernd Knabe, Kelkheim, Taunus; Hans-Jochen Lang, Altenhain, Taunus; Milos Babej; Roman Muschaweck, both of Frankfurt am Main, all of Germany

[73] Assignee: Hoechst Aktiengesellschaft, Frankfurt am Main, Germany

[22] Filed: Jan. 21, 1975

[21] Appl. No.: 542,699

[30] Foreign Application Priority Data

Jan. 23, 1974 Germany .......................... 2403138

[52] U.S. Cl. .............................. 424/282; 260/340.5; 260/570.9
[51] Int. Cl.² ....................................... A61K 31/36
[58] Field of Search .............. 260/340.5 R; 424/282

[56] References Cited
OTHER PUBLICATIONS
Chem. Abstracts, 49:6141h.

*Primary Examiner*—Ethel G. Love
*Attorney, Agent, or Firm*—Curtis, Morris & Safford

[57] ABSTRACT

N-Cycloalkyl-benzylamine derivatives of the formula

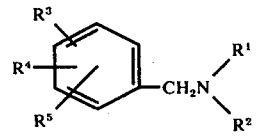

in which $R^1$ represents hydrogen or lower alkyl of 1 to 4 carbon atoms, $R^2$ represents a cycloalkyl radical of a total of 7 to 12 carbon atoms which may be alkyl-substituted and may contain hydrocarbon bridges of 1 to 3 carbon atoms, $R^3$ represents hydrogen, alkoxy of 1 to 4 carbon atoms, $R^4$ represents hydrogen or alkoxy of 1 to 4 carbon atoms or halogen, and $R^5$ represents alkoxy of 1 to 4 carbon atoms, methylene dioxy, ethylene dioxy, benzyloxy or halogen, and the physiologically tolerated salts thereof are disclosed as having diuretic and saluretic activity.

7 Claims, No Drawings

BENZYLAMINE DERIVATIVES AND PROCESS FOR PREPARING THEM

The present invention relates to novel benzylamine derivatives of the formula I

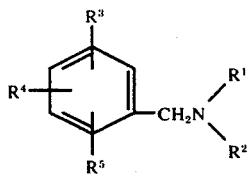

in which $R^1$ represents hydrogen or lower alkyl of 1 to 4 carbon atoms, $R^2$ represents a cycloalkyl radical of a total of 7 to 12 carbon atoms which may be alkyl-substituted and may contain hydrocarbon bridges of 1 to 3 carbon atoms, $R^3$ represents hydrogen, alkoxy of 1 to 4 carbon atoms, $R^4$ represents hydrogen, alkoxy of 1 to 4 carbon atoms or halogen, and $R^5$ represents alkoxy of 1 to 4 carbon atoms, methylene dioxy, ethylene dioxy, benzyloxy or halogen, and their physiologically tolerated salts.

The invention furthermore relates to a process for preparing the above-identified benzylamines of the formula I and of their physiologically tolerated salts, which comprises a. condensing aldehydes of the formula II

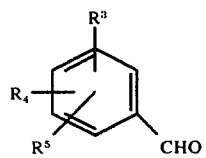

in which $R^3$, $R^4$ and $R^5$ have the meanings given above, with primary amines of the formula III

in which $R^2$ has the meaning given above, and reducing the aldimines so obtained to the corresponding amines, or b. reducing aldehydes of the formula II in the presence of amines of the formula III, in which $R^2$, $R^3$, $R^4$ and $R^5$ have the meanings given above, or c. reacting amines of the formula IV

in which $R^1$ and $R^2$ have the meanings given above, with a benzylating agent of the formula V

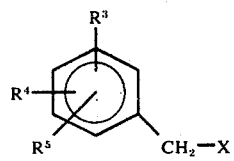

in which $R^3$, $R^4$ and $R^5$ have the meanings given above and X represents a group which reacts by nucleophilic substitution, for example halogen, the radical of a reactive ester, a quarternary ammonium group, or d. reducing benzylamines of the formula VI

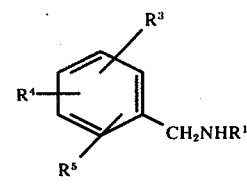

in which $R^1$, $R^3$, $R^4$ and $R^5$ have the meanings given above, in the presence of ketones of the formula VII

in which $R^6$ and $R^7$ are members of a carbocyclic ring system of 7 to 12 carbon atoms, which may be alkyl-substituted and which may contain hydrocarbon bridges of 1 to 3 carbon atoms, or e. reducing carboxylic acid amides of the formula X

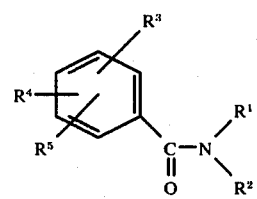

in which $R^1$ to $R^5$ have the meanings given above, to the corresponding amines, or f. reacting phenols of the formula XI

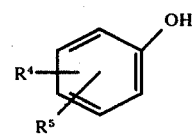

with formaldehyde and an amine of the formula IV and further reacting the hydroxybenzylamines of the formula XII

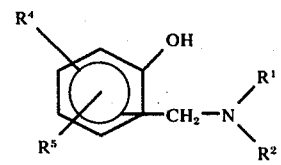

in which $R^1$, $R^2$, $R^4$ and $R^5$ have the meanings given above, optionally in the form of the corresponding phenolate, with an alkylating agent of the general formula XIII

in which $R^8$ represents alkyl of 1 to 4 carbon atoms and X represents a nucleophilically substitutable grouping, for example halogen, the rest of a reactive ester or of a quaternary ammonium compound, and optionally treating the compounds obtained according to methods (a) to (f), in which $R^1$ represents hydrogen and $R^2$ to $R^5$ have the meanings given above, with alkylating agents and/or transforming the compounds so obtained into their salts with physiologically tolerated acids.

The synthesis of the compounds of the formula I is carried out according to methods known in the preparation of secondary amines.

For the preparation of the novel compounds of the general formula I according to the methods described inder (1) and (2), there may be used, as aldehydes, the following compounds which are well known and may be easily prepared according to known methods (cf. Houben-Weyl, Vol. 7/1):

2-chlorobenzaldehyde, 2,4-dichlorobenzaldehyde, 2,6-dichlorobenzaldehyde, 3-chlorobenzaldehyde, 4-chlorobenzaldehyde, 2-methoxy-benzaldehyde, 3-methoxy-benzaldehyde, 4-methoxy-benzaldehyde, 3-methoxy-4-chlorobenzaldehyde, 3-chloro-4-methoxy-benzaldehyde, 2-chloro-3-methoxy-benzaldehyde, 2-bromobenzaldehyde, 3-methoxy-4-bromo-benzaldehyde, 2-bromobenzaldehyde, 3-methoxy-4-benzaldehyde, 3-benzyloxy-4-chlorobenzaldehyde, 3-chloro-4-methylbenzaldehyde, 3-methyl-4-bromobenzaldehyde, 2-chloro-6-methylbenzaldehyde, 3,5-dichloro-4-methyl-benzaldehyde, piperonal, 3,4-ethylene-dioxybenzaldehyde, 2,4-dimethoxy-benzaldehyde, 2,4-dibutoxybenzaldehyde, 2,5-dimethoxy-benzaldehyde, 2,6-dimethoxybenzaldehyde, 2,6-diethoxybenzaldehyde, 2,4,6-trimethoxy-benzaldehyde, 3,4,5-trimethoxy-benzaldehyde, 2,4,5-timethoxybenzaldehyde, 3-methyl-4-benzyloxy-benzaldehyde, 3-methyl-4-ethoxybenzaldehyde, 3-methyl-4-propoxybenzaldehyde, 3-methyl-4-butoxybenzaldehyde, 2,6-dimethoxy-4-methylbenzaldehyde, 2,6-diethoxy-4-methylbenzaldehyde, 2,4-dimethoxy-3-methylbenzaldehyde, 2,4-dibutoxy-3-methyl-benzaldehyde, 3-ethyl-4-methoxy-benzaldehyde, 3-ethyl-4-benzyloxybenzaldehyde, 3-methyl-6-methoxy-benzaldehyde, 3-methyl-6-benzyloxy-benzaldehyde, 2,4-dimethoxy-5-methyl-benzaldehyde, 3-methoxy-4-butoxy-benzaldehyde.

The amines of the formula III are likewise well known from literature (cf. Houben-Weyl, Vol X/1). Examples thereof are:

cycloheptylamine, cyclooctylamine, cyclononylamine, cyclodecylamine, cycloundecylamine, cyclododecylamine, 1-adamantylamine, 2-adamantylamine, tricyclo[5,2,1,0$^{2,6}$]-decane-8-yl-amine, norcarane-7-yl-amine, tricyclo[5,2,1,0$^{2,6}$]-decane-4-yl-amine, bicyclo[3,2,1]-octane-6-yl-amine, bicyclo[2,2,2]-octane-yl-amine, bornylamine, fenchylamine, nortricyclyl-3-amine.

The reduction of the aldehydes II in the presence of amines of formula III is carried out advantageously by catalytical hydrogenation. As catalysts, there are used metals of the VIII. Group of the Periodical system, preferably noble metals. The reaction is suitably carried out in the presence of solvents which are appropriate for such purposes, for example aqueous alcohols, alcohols or water.

There may also be used nickel catalysts, preferably Raneynickel catalysts. The reduction may also be effected with the aid of sodium boron-hydride by first preparing the condensation product of amine and aldehyde optionally at slightly elevated temperatures and optionally in the presence of an inert organic solvent, for example benzene or toluene, and optionally of a small amount of dimethylformamide (DMF) and optionally with addition of an acid catalyst, for example p-toluene-sulfonic acid, and after dilution with a suitable solvent, for example a lower alcohol, optionally in the presence of water, reducing it by the addition of sodium boron-hydride. Furthermore, the reduction may also be carried out with hydrogen in statu nascendi, for example with sodium amalgam and alcohol or aluminium amalgam. The more, the reduction may also be effected electrolytically. In some cases, it may be of advantage first to isolate the condensation product obtained from the aldehyde II and amine III and then to reduce in the second reaction stage.

The condensation effected in the first stage generally succeeds already at room temperature or at a slightly elevated temperature (steam bath).

It is suitable to operate in the presence of inert organic solvents such as benzene or toluene, optionally also with the addition of a small amount of dimethylformamide and of an acid catalyst, for example HCl, $H_2SO_4$ or p-toluene-sulfonic acid. For the reduction, it is of advantage to use one of the afore-mentioned solvents and to proceed as indicated.

According to another advantageous method of operation (b), the above-mentioned amines of the formula III may be reacted, for example, with a benzylating agent of the formula V by methods known in literature. This reaction is suitably carried out in appropriate solvents, for example in aromatic hydrocarbons such as benzene or toluene, as well as in lower alcohols, for example methanol or ethanol, by prolonged heating.

When using benzyl halides as benzylating agents of the general formula V, there may be reacted, for example 1 mole of benzyl halide with 2 moles of amine III in order to bind the hydrohalide set free.

Binding of the hydrohalic acid may be effected with the usual basic agents such alkali metal and alkaline earth metal carbonates or hydroxides, as well as with organic bases such as pyridine or quinoline, which may simultaneously serve as solvent. Working up is carried out in the usual manner by separation of the hydrohalic salt of the base used, for example by precipitation with ether or extraction with water. The basic product may then be purified by distillation or by transformation into a suitable salt. If desired, the compounds obtained may be N-alkylated in the above-described manner.

According to another variant of the process (c), the benzylamines of the general formula VI may be reduced in the presence of ketones of the general formula VII. The benzylamines of the general formula VI can be easily prepared according to known methods. As starting product, there may be used, for example, the aldehydes cited on pages 5 and 6. The ketones of formula VII are well known from literature. Some special examples thereof are, for example:

cycloheptanone, cyclooctanone, cyclononanone, cyclodecanone, cycloundecanone, cyclododecanone, bicyclo [3,2,1]-octane-6-one, fenchone, 2-bornanone, tricyclo[2,2,1,0$^{2,6}$]heptane-3-one, bicyclo[2,2,2]-octane-2-one, bicyclo[3,2,1]-octane-2-one.

The reactions yielding the benzylamines of the general formula I is generally carried out under the reaction conditions specified for method (a). Accordinng to method (e), it is also possible to prepare according to methods known in literature using the amines of the formula III carboxylic acid amides of the general formula X which are then reduced to the novel products of the invention. The reduction is carried out in known manner with complex metal hydrides, the use of lithium-aluminium hydride being particularly advantageous. The reduction of the carboxylic acid amides with the aid of lithium-aluminum hydride is carried out according to methods known per se suitably in the presence of inert organic solvents such as ether, dioxane or tetrahydrofurane. It is advantageous to add the amide to the lithium-aluminum hydride suspension in one of the mentioned solvents, to allow the reaction mixture to boil for some time under reflux, decomposing it with precaution with water and to work up in the usual manner by separating the organic components from the inorganic components.

Furthermore, the reduction of the carbonamides described to the amines may also be effected by electrolysis.

Finally, there may be converted according to method (f), phenols of the general formula XI in known manner with formaldehyde and an amine of the general formula IV at first to the hydroxybenzylamines of the general formula XII which are then converted into the products of the invention using an alkylating agent of the general formula XIII. The reaction to the hydroxybenzylamines of the formula XII may also be carried out by combining the pure components as well as in non-polar or polar solvent at temperatures between 0° and 150° C. It is preferred to use a secondary amine and to operate suitably in water or in a lower alcohol at an elevated temperature, preferably at between 50° and 100° C.

For the following O-alkylation, the hydroxybenzylamine of the formula XII is reacted preferably in the presence of a sufficiently strong base, for example in the presence of hydroxide, hydride or alcoxide ions, an amine, etc., with a suitable alkylating agent, for example an alkyl halide, a sulfuric acid ester, an organosulfonic acid alkyl ester, or tetra-alkylammonium salts. The corresponding phenolate is then reacted with the alkylating agent, optionally at an elevated temperture, in the form of the pure components or, preferably, in a polar solvent, for example in alcohol, DMF, DMSO.

The amines obtained according to methods (a) to (f) may be N-alkylatedin known manner (cf. for example Houben-Weyl, Vol. XI/1) using the usual alkylating agents, for example alkyl halides, alkyl sulfates, alkyl tosylates or alkylammonium compounds. Another advantageous method of operation consists in reductively alkylating the amines or reacting them under the conditions of the Leuckart-Wallach reaction.

The reductive alkylation is suitably carried out in an appropriate solvent such as methanol or ethanol, at a hydrogen pressure of 20 to 150 atmospheres gauge and a temperature of 40° to 150° C. As catalysts, there are preferably used Raney nickel or platinum metals.

As basic compounds, the products of the invention may be converted into the corresponding salts with the aid of inorganic or organic acids. As inorganic acids, there may be used, for example hydrohalic acids such as hydrochloric acid and hydrobromic acid, furthermore sulfuric acid, phosphoric acid and amidosulfonic acid.

As organic acids, there may be mentioned, for example formic acid, acetic acid, propionic acid, lactic acid, glycolic acid, gluconic acid, maleic acid, succinic acid, tartaric acid, benzoic acid, salicylic acid, citric acid, aceturic acid, oxethane-sulfonic acid and ethylenediaminotetracetic acid.

The products of the invention are valuable medicaments and are distinguished, in particular, by a very good diuretic and saluretic activity.

A diuretic and saluretic action by benzylamines has been described in some patent specifications (c.f., for example U.S. Pat. No. 3,080,365). These known compounds are benzylamines with a phenolic hydroxy group, the benzylamino radical being free, N-alkylated or N-acylated, or N-acylated benzylamines. It is therefore surprising that the novel products of the invention with voluminous N-cycloalkyl groups have very good diuretic and saluretic properties.

Tests on rats for diuretic and saluretic activity have shown that the products of the invention are clearly superior to the 5-piperidinomethyl-eugenol-hydrochloride described as diuretic agent (cf. U.S. Pat. No. 3,080,365) and that likewise in comparison with the commercial preparations Hydrochlorothiazide and Chlorothalidon they have very good diuretic and saluretic activities. In addition thereto, their low potassium elimination which is expressed in considerably higher sodium/potassium quotients, is of particular therapeutic advantage. These quotients are so favourable that when these compounds are used in therapy it can be expected not to be necessary to use additional measures (potassium substitution, combination with potassium-retaining substances).

Owing to their favourable properties, the products of the invention are valuable medicaments for human beings in the therapy of edemas and, when combined with other compounds having a hypotensive action, in the permanent therapy of essential hypertonia.

The compounds of the invention are preferably administered perorally.

As preparations which contain the compounds of the invention and which may be used in therapy, there enter into consideration above all tablets, dragees and capsules. Preferably, these preparations contain the compounds of the invention in the form of hydrochlorides. The therapeutic unit does of active substance in these preparations is in the range of from 5 to 500 mg.

Preparations containing 20 to 100 mg of the active ingredient may be administered to human beings once or several times per day.

The following Examples illustrate the invention.

EXAMPLE 1

8.25 g of piperonal and 7.55 g of 1-adamantylamine were boiled for 3 hours on a water separator in 200 ml of benzene and 25 ml of dimethylformamide (DMF) in the presence of a catalytical amount of p-toluenesulfonic acid. The residue remaining behind after removal of the solvent was reduced in 250 ml of methanol at normal temperature with 2.5 g of NaBH$_4$.

After having stirred the whole for 1 hour at room temperature, the reaction mixture was acidified with methanolic HCl, filtered and the filtrate was concentrated by evaporation. 11.2 g of N-adamantyl-(1)-3,4-methylenedioxy-benzylamine-hydrochloride with a melting point of 279°–280° C (from ethanol/ether) were obtained.

EXAMPLE 2

Starting from 10.8 g of 3,4,5-trimethoxybenzaldehyde and 7.55 g of 1-adamantylamine, there were obtained according to the method described in Example 1 13 g of N-adamantyl-(1)-3,4,5-trimethoxy-benzylamine-hydrochloride. Melting point 243°–244° C (from ethanol/ether).

EXAMPLE 3

Starting from 13.5 g of 3-benzyloxy-4-chlorobenzaldehyde and 7.55 g of 1-adamantylamine, there were obtained according to the method described in Example 1 12.5 g of N-adamantyl-(1)-3-benzyloxy-4-chlorobenzylamine-hydrochloride. Melting point 230° C (from ethanol/ether).

EXAMPLE 4

Starting from 7.75 g of p-chlorobenzaldehyde and 7.55 g of 1-adamantylamine, there were obtained according to the method described in Example 1 7,2 g of N-adamintyl-(1)-4-chlorobenzylamine hydrochloride. Melting point 316°–318° C (dec.)(from ethanol/ether).

EXAMPLE 5

Starting from 7.75 g of 2-chlorobenzaldehyde and 7.55 g of 1-adamantylamine, there were obtained according to the method described in Example 1 13.3 g of N-adamantyl-(1)-2-chlorobenzylamine hydrochloride. Melting point 269°–271° C (from ethanol/ether).

EXAMPLE 6

Starting from 8.25 g of piperonal and 6.35 g of cyclooctylamine, there were obtained according to the method described in Example 1, 7.9 g of N-cyclooctyl-3,4-methylene-dioxy-benzylamine hydrochloride. Melting point 164°–165° C (from ethanol/ether).

EXAMPLE 7

16.5 g of piperonal, 12,7a g of cyclooctylamine and a catalytical amount of p-toluene-sulfonic acid were hydrogenated for 6 hours in 500 ml of methanol over Raney nickel at 100° C/100 atmospheres gauge pressure. After removal of the catalyst, evaporation of the solution and treatment of the residue with methanolic HCl, there were obtained 23 g of N-cyclooctyl-3,4-methylenedioxy-benzylamine. Melting point 164°–165° C (from ethanol/ether).

EXAMPLE 8

Starting from 10.8 g of 3,4,5-trimethoxybenzaldehyde and 6.35 g of cyclooctylamine, there were obtained according to the method described in Example 1 13.5 g of N-cyclooctyl-3,4,5-trimethoxybenzylamino-hydrochloride. Melting point 131°–132° C (from ethanol/ether).

EXAMPLE 9

Starting from 8.25 g of piperonal and 7.55 g of tricyclo-[5,2,1,] [5,2,1,0$^{2,6}$]-decane-8-yl-amine, 11.2 g of N-tricyclo-[5,2,1,0$^{2,6}$]-decane-8-yl-3,4-methylene-dioxy-benzylamine-hydrochloride, Melting point 216°–217° C (from ethanol/ether).

EXAMPLE 10

Starting from 9.15 g of 3,4-dimethoxybenzaldehyde and 7.55 g of 1-adamantyl-amine, there were obtained according to the method described in Example 1 11.2 g of N-adamantyl-(1)-3,4-dimethoxybenzylamine-hydrochloride. Melting point 286°–287° C (from ethanol).

EXAMPLE 11

Starting from 9.62 g of 2,6-dichlorobenzaldehyde and 7.05 g of 1-adamantylamine, there were obtained according to the method described in Example 1 2 g of N-adamantyl-(1)-2,6-dichlorobenzylamine-hydrochloride. Melting point 290° C (from ethanol/ether).

EXAMPLE 12

Starting from 8.25 g of piperonal and 9.15 g of cyclododecylamine, there were obtained according to the method described in Example 1 10.8 g of N-cyclododecyl-3,4-methylenedioxybenzylamine-hydrochloride. Melting point 171° C (from ethanol/ether).

EXAMPLE 13

Starting from 7.55 g of p-methoxybenzaldehyde and 7.55 g of 1-adamantylamine, there were obtained according to the method described in Example 1 9 g of N-adamantyl-(1)-4-methoxy-benzylamine. Melting point 283°–284° C (from ethanol/ether).

EXAMPLE 14

Starting from 9.15 g of 3.4-dimethoxybenzaldehyde and 7.55 g of tricyclo[4,2,1,0$^{2,6}$]decane-8-yl-amine, there were obtained according to the method described in Example 1 12 g of N-tricyclo[5,2,1,0$^{2,6}$]decane-8-yl-3,4-dimethoxy-benzylamine hydrochloride. Melting point 186°–187° C (from ethanol/ether).

EXAMPLE 15

Starting from 9.2 g of 3,4-dimethoxybenzaldehyde and 6,4 g of cyclooctylamine, there were obtained according to the method described in Example 1 10.1 g of N-cyclooctyl-3,4-dimethoxybenzylamine-hydrochloride. Melting point 162°–163° C (from ethanol/ether).

EXAMPLE 16

Starting from 7.54 g of 3-methoxybenzaldehyde and 7.55 g of 1-adamantylamine, there were obtained according to the method described in Example 1 9.7 g of N-adamantyl-(1)-3-methoxybenzylamine-hydrochloride. Melting point 274°–276° C (from ethanol/ether).

EXAMPLE 17

5.7 g of N-adamantyl-(1)-3,4-methylene-dioxybenzylamine (cf. Example 1) were heated for 24 hours to 100°–110° C with 20 ml of 98% formic acid and 20 ml of 40% aqueous formaldehyde. The reaction solution was concentrated, the residue was dissolved in hot water, if necessary filtered over charcoal and acidified with concentrated HCl. After evaporation of the solution, 3 g of N-methyl-N-adamantyl-(1)-3,4-methylenedioxybenzylamine hydrochloride were obtained. Melting point 226°–227° C (from ethanol/ether).

EXAMPLE 18

Starting from 5.7 g of N-tricyclo-[5,2,1,0$^{2,6}$]decane-8-yl-3,4-methylenedioxybenzylamine, there were obtained according to the method described in Example 17 4.1 g of N-methyl-N-tricyclo-[5,2,1,0$^{2,6}$]decane-8-yl-3,4-methylene-dioxybenzylamine-hydrochloride. Melting point 240°–241° C (from ethanol/ether).

EXAMPLE 19

Starting from 4 g of N-cyclooctyl-3,4-methylenedioxybenzylamine, there were obtained according to the method described in Example 17 3.7 g of N-methyl-N-cyclooctyl-3,4-methylene-dioxybenzylamine-hydrochloride. Melting point 215°–216° C (from ethanol/ether).

EXAMPLE 20

Starting from 6 g of N-adamantyl-(1)-3,4-dimethoxybenzylamine, there were obtained according to the method described in Example 17 3.8 g of N-methyl-N-adamantyl-3,4-dimethoxy-benzylamine-hydrochloride. Melting point 224°–225° C (from ethanol/ether).

EXAMPLE 21

Starting from 6 g of N-tricyclo[5,2,1,0$^{2,6}$]decane-8-yl-3,4-dimethoxy-benzylamine, there were obtained according to the method described in Example 17 5.4 g of N-methyl-N-tricyclo[5,2,1,0$^{2,6}$]-decane-8-yl-3,4-dimethoxy-benzylamine-hydrochloride. Melting point 202°–203° C (from ethanol/ether).

EXAMPLE 22

Starting from 5.5 g of N-adamantyl-(1)-2-chlorobenzylamine, there were obtained according to the method described in Example 17 3.9 g of N-methyl-N-adamantyl-2-chlorobenzylamine-hydrochloride. Melting point 224°–225° C (from ethanol/ether).

EXAMPLE 23

Starting from 6.6 g of N-cyclooctyl-3,4-dimethoxybenzylamine, there were obtained according to the method described in Example 17 4.5 g of N-methyl-N-cyclooctyl-3,4-dimethoxy benzylamine-hydrochloride. Melting point 187°–188° C (from ethanol/ether).

EXAMPLE 24

Starting from 6.7 g of N-adamantyl-(1)-3-benzyloxy-4-chlorobenzylamine, there were obtained according to the method described in Example 17 4.3 g of N-methyl-N-adamantyl-(1)-3-benzyloxy-4-chlorobenzylamine-hydrochloride. Melting point 212°–213° C (from ethanol/ether).

EXAMPLE 25

Starting from 6 g of N-adamantyl-(1)-4-methoxybenzylamine, there obtained according to the method described in Example 17 3.9 g of N-methyl-N-adamantyl-4-methoxy-benzylamine-hydrochloride. Melting point 229°–230° C (from ethanol/ether).

EXAMPLE 26

Starting from 7.5 g of m-methoxybenzaldehyde and 7.55 g of tricyclo[5,2,1,0$^{2,6}$]decane-8-yl-amine, there were obtained according to the method described in Example 1 11.2 g of N-tricyclo[5,2,1,0$^{2,6}$]decane-8-yl-m-methoxybenzylamine-hydrochloride. Melting point 193°–194° C (from ethanol/ether).

EXAMPLE 27

Starting from 7.8 g of o-chlorobenzaldehyde and 7.55 g of tricyclo[5,2,1,0$^{2,6}$]decane-8-yl-amine, there were obtained according to the method described in Example 1 10.8 g of N-tricyclo[5,2,1,0$^{2,6}$]decane-8-yl-o-chlorobenzylamine-hydrochloride. Melting point 222°–223° C (from ethanol/ether).

EXAMPLE 28

Starting from 7.8 g of o-chlorobenzaldehyde and 6.35 g of cyclooctylamine, there were obtained according to the method described in Example 1 5.2 g of N-cyclooctyl-2-chlorobenzylamine-hydrochloride. Melting point 201° C (from ethanol/ether).

EXAMPLE 29

Starting from 7.8 g of o-chlorobenzaldehyde and 9.15 g of cyclododecylamine, there were obtained according to the method described in Example 1 11.4 g of N-cyclododecyl-o-chlorobenzylamine-hydrochloride. Melting point 194°–195° C (from ethanol/ether).

EXAMPLE 30

Starting from 9.15 g of 3,4-dimethoxybenzaldehyde and 9.15 g of cyclododecylamine, there were obtained according to the method described in Example 1 13.9 g of N-cyclododecyl-3,4-dimethoxybenzylamine-hydrochloride. Melting point 178°–179° C (from ethanol/ether).

EXAMPLE 31

Starting from 13.6 g of 3-benzyloxy-4-chlorobenzaldehyde and 7.55 g of tricyclo-[5,2,1,0$^{2,6}$]decane-8-yl-amine, there were obtained according to the method described in Example 1 6.3 g of N-tricyclo-[5,2,1,0$^{2,6}$]decane-8-yl-m-benzyloxy-p-chlorobenzylamine-hydrochloride. Melting point 170°–171° C (from ethanol/ether).

EXAMPLE 32

Starting from 8.84 g of 2,4-dichlorobenzaldehyde and 7.55 g of 1-adamantylamine, there were obtained according to the method described in Example 1 6.5 g of N-adamantyl-(1)-2,4-dichlorobenzylamine-hydrochloride. Melting point 262°–263° C (from ethanol/ether).

EXAMPLE 33

Starting from 9.9 g of 3-methoxy-4-chlorobenzaldehyde and 7.55 g of 1-adamantylamine, there were obtained according to the method described in Example 1 8 g of N-adamantyl-(1)-3-methoxy-4-chloro-benzylamine-hydrochloride. Melting point 301°–302° C (from ethanol).

EXAMPLE 34

Starting from 9.9 g of 3-methoxy-4-chlorobenzaldehyde and 6.35 g of cyclooctylamine, there were obtained according to the method described in Example 1 7.2 g of N-cyclooctyl-3-methoxy-4-chloro-benzylamine-hydrochloride. Melting point 222°–223° C (from ethanol).

EXAMPLE 35

Starting from 6.25 g of N-tricyclo[5,2,1.0$^{2,6}$]decyl-(8)-2'-chlorobenzylamine, there were obtained according to the method described in Example 17 3.5 g of N-methyl-N-tricyclo[5,2,1,0$^{2,6}$]-decyl-(8)-2'-chlorobenzylamine-hydrochloride. Melting point 184°–185° C (from ethanol/ether).

EXAMPLE 36

Starting from 5.5 g of N-cyclooctyl-2-chlorobenzylamine, there were obtained according to the method described in Example 17 2.8 g of N-methyl-N-cyclooctyl-2-chlorobenzylamine-hydrochloride. Melting point 176°–178° C (from ethanol/ether).

EXAMPLE 37

Starting from 7.0 g of N-cyclododecyl-3,4-dimethoxy-benzylamine, there were obtained according to the method desscribed in Example 17 3.3 g of N-methyl-N-cyclododecyl-3,3-dimethoxybenzylamine-hydrochloride. Melting point 153°–154° C (from ethanol/ether).

EXAMPLE 38

Starting from 5 g of N-cyclooctyl-3-methoxy-4-chlorobenzylamine, there were obtained according to the method described in Example 17 4 g of N-methyl-N-cyclooctyl-3-methoxy-4-chlorobenzylamine-hydrochloride. Melting point 190°–191° C (from ethanol/ether).

EXAMPLE 39

Starting from 6.4 g of N-cyclododecyl-2-chlorobenzylamine, there were obtained to the method described in Example 17 1.9 g of N-methyl-N-cyclododecyl-2-chlorobenzylamine-hydrochloride. Melting point 145°–147° C (from ethanol/ether).

EXAMPLE 40

Starting from 6 g of N-adamantyl-(1)-3-methoxy-4-chlorobenzylamine, there were obtained according to the method described in Example 17 1.3 g of N-methyl-N-adamantyl-(1)-3-methoxy-4-chlorobenzylamine-hydrochloride. Melting point 236°–237° C (from ethanol/ether).

EXAMPLE 41

The reaction mixture of 3.15 g of 3-methoxy-benzylchloride, 3.0 g of 1-adamantylamine and 2 g of triethylamine in 30 ml of absolute ethanol was stirred for 15 minutes at room temperature and then heated for 4 hours to reflux temperature. After concentration, the residue was treated with 40 ml of 6N-HCl, whereupon 2.5 g of N-adamantyl-(1)-3-methoxy-benzylamine-Hydrochloride were obtained, Melting point 274°–276° C (from ethanol/ether).

EXAMPLE 42

A solution of 5.0 g of 3,4-dimethoxy-benzoic acid cyclooctylamide in 20 ml of absolute THF was added dropwise to a suspension of 1.4 g of lithium-aluminium hydride in 30 ml of absolute THF, the reaction mixture was heated for 4 hours to the boiling temperature and, after having cooled, it was cautiously combined with water. The residue was treated with 50 ml of THF, the combined organic phases were dried over $Na_2SO_4$, the solvent was removed and the oil obtained was combined with methanolic hydrochloric acid. After concentration, 3.9 g of N-cyclooctyl-3,4-dimethoxy-benzylamine-hydrochloride were obtained. Melting point 161°–163° C (from ethanol/ether).

EXAMPLE 43

Starting from 4.0 g of 3-methyl-4-methoxy-benzaldehyde and 4.5 g of 1-adamantylamine, there were obtained according to the method described in Example 1 6.0 g of N-adamantyl-(1)-3-methyl-4-methoxy-benzylamine-hydrochloride. Melting point 283°–284° C (from ethanol/ether).

EXAMPLE 44

Starting from 6.7 g of 3-methyl-4-methoxy-benzaldehyde and 6.4 g of cyclooctylamine, there were obtained according to the method described in Example 1 10.8 g of N-cyclooctyl-3-methyl-4-methoxy-benzylamine-hydrochloride. Melting point 174°–175° C (from ethanol/ether).

EXAMPLE 45

Starting from 4.9 g of 3,4-ethylene-dioxy-benzaldehyde and 4.5 g of 1-adamantylamine, there were obtained according to the method described in Example 1 6.3 g of N-adamantyl-(1)-3,4-ethylenedioxy-benzylamine-hydrochloride. Melting point 308°–304° C (from ethanol/ether).

EXAMPLE 46

Starting from 3.3 g of 3,4-ethylenedioxy-benzaldehyde and 2.6 g of cyclooctylamine, there were obtained according to the method described in Example 1 4.1 g of N-cyclooctyl-3,4-ethylenedioxy-benzylamine-hydrochloride. Melting point 167°–169° C (from ethanol).

EXAMPLE 47

Starting from 3.9 g of 2,3,4-trimethoxy-benzaldehyde and 3.0 g of 1-adamantylamine, there were obtained according to the method described in Example 1 3.0 g of N-adamantyl-(1)-2,3,4-trimethoxy-benzylamine-hydrochloride. Melting point 216°–218° C (from ethanol/ether).

EXAMPLE 48

Starting from 4.5 g of 3-chloro-4-methyl-benzaldehyde and 3.9 g of cyclooctylamine, there were obtained according to the method described in Example 1 7.1 g of N-cyclooctyl-3-chloro-4-methyl-benzylamine-hydrochloride. Melting point 212°–213° C (from ethanol/ether).

EXAMPLE 49

Starting from 5.4 g of cyclooctyl-3-methyl-4-methoxy-benzylamine, there were obtained according to the method described in Example 17 4.9 g of N-methyl-N-cyclooctyl-3-methyl-4-methoxy-benzylamine-hydrochloride. Melting point 216°–218° C (from ethanol/ether).

EXAMPLE 50

Starting from 6.8 g of N-cyclooctyl-3-chloro-4-methyl-benzylamine, there were obtained according to the method described in Example 17 4.9 g of N-methyl-N-cyclooctyl-3-chloro-4-methylbenzylamine-hydrochloride. Melting point 248°–250° C (from ethanol/ether).

EXAMPLE 51

Starting from 4.5 g of 3-chloro-4-methyl-benzaldehyde and 4.5 g of 1-adamantylamine, there were obtained according to the method described in Example 1 5.0 g of N-adamantyl-(1)-3-chloro-4-methyl-benzylamine-hydrochloride. Melting point 345° C (from ethanol/ether).

EXAMPLE 52

15.1 g of 3,4-methylenedioxybenzylamine and 18.2 g of cyclododecanone wre hydrogenated at 90° C and a pressure of 100 atmospheres gauge in the presence of Raney nickel until the absorption of hydrogen ceased. After concentration, the residue was acidified with 2N-hydrochloric acid, whereupon 17.5 g of N-cyclododecyl-3,4-methylene-dioxybenzylamine-hydrochloride were obtained.

Melting point 171° C (ethanol/ether).

EXAMPLE 53 a. 14.2 g of 3-chloro-4-hydroxytoluene in 50 ml of water were combined successively with 14.5 g of N-cyclooctylmethylamine and 10 ml of 35% aqueous formaldehyde solution and the whole was heated for 2 hours under reflux. After extraction with diethyl ether, drying of the organic phase over sodium sulfate and evaporation of the solvent, 22 g of 2-hydroxy-3-chloro-5-methyl-N-methyl-N-cyclooctyl-benzylamine were obtained. Melting point 101° C (from diisopropyl ether).

b. 7.4 g of 2-hydroxy-3-chloro-5-methyl-N-methyl-N-cyclooctylbenzylamine were dissolved in 40 ml of hot absolute ethanol and added to a sodium ethylate solution that had been prepared from 0.6 g of sodium in 25 ml of absolute ethanol. After addition of 4.5 g of benzenesulfonic acid ethyl ester, the whole was stirred for 5 hours under reflux, concentrated, the residue was dissolved in 50 ml of 5% sodium hydroxide solution, extracted with ether and the organic phase was dried over sodium sulfate. The solvent was removed and after addition of 70 ml of water and hydrochloric acid until acid reaction the residue was covered with 50 ml of ether and allowed to stand for several days at 0° C. In this manner, 6 g of 2-ethoxy-3-chloro-5-methyl-N-methyl-N-cyclooctyl-benzylamine-hydrochloride were obtained. Melting point 197° C (ethanol/ether).

EXAMPLE 54

Starting from 16.6 g of 2,4-dimethoxybenzaldehyde and 15.1 g of 1-adamantylamine, there were obtained according to the method described in Example 1 22 g of 2,4-dimethoxy-N-adamantyl-(1)-benzylamine-hydrochloride. Melting point 252° C (from nitromethane).

EXAMPLE 55

Starting from 16.6 g of 2,4-dimethoxy-benzaldehyde and 18.3 g of cyclododecylamine, there were obtained according to the method described in Example 1 32 g of 2,4-dimethoxy-N-cyclododecyl-benzylamine-hydrochloride. Melting point 179° C (from nitromethane).

EXAMPLE 56

Starting from 6.55 g of 3-methyl-4-ethoxy-benzaldehyde and 6.0 g of 1-adamantlyamine, there were obtained according to the method described in Example 1 9.46 g of 3-methyl-4-ethoxy-N-adamantyl-(1)-benzylamine-hydrochloride. Melting point 263°–264° C (from ethanol).

EXAMPLE 57

Starting from 6.55 g of 3-methyl-4-ethoxy-benzaldehyde and 5.1 g of cyclooctylamine, there were obtained according to the method described in Exaple 1 6.5 g of 3-methyl-4-ethoxy-N-cyclooctyl-benzylamine-hydrochloride. Melting point 165°–166° C (from ethyl acetate).

EXAMPLE 58

9.0 g of N-1-adamantylamine-3,4-dimethoxy-benzylamine were heated with 4.62 g of diethyl-sulfate for 22 hours to 100° C. The mixture was treated with a solution of 2.1 g of potassium hydroxide in 20 ml of water, decanted and the residue was combined with a solution of 2.1 g of potassium hydroxide in 200 ml of water and 50 ml of ethanol. The whole was extracted with ether, the ether extracts were dried over sodium sulfate and the solvent was removed by rotation. The remaining oil was combined with hydrochloric acid and the mixture was evaporated to dryness. In this manner 5.9 g of N-adamantyl-(1)-N-ethyl-3,4-dimethoxy-benzylamine-hydrochloride were obtained; after recrystallization from ethanol/ether, the compound was found to melt at 233°–225° C.

EXAMPLE 59

Starting from 4 g of 3-methyl-4-methoxy-benzaldehyde and 4 g of tricyclo[5,2,1,0$^{2,6}$]decane-8-yl-amine, there were obtained according to the method described in Example 1 6.2 g of N-tricyclo[5,2,1,0$^{2,6}$]decane-8-yl-3-methyl-4-methoxy-benzylamine-hydrochloride. Melting point 228°–230° C (from ethanol/ether).

We claim:

1. A benzylamine of the formula

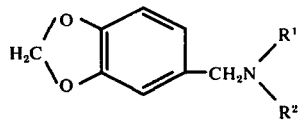

wherein R$^1$ is hydrogen or methyl and R$^2$ is adamantyl or cyclooctyl.

2. A compound as claimed in claim 1, which is N-adamantyl-(1)-3,4-methylenedioxy-benzylamine-hydrochloride.

3. A compound as claimed in claim 1, which is N-cyclooctyl-3,4-methylenedioxy-benzylamine-hydrochloride.

4. A compound as claimed in claim 1, which is N-methyl-N-adamantyl-(1)-3,4-methylenedioxybenzylamine-hydrochloride.

5. A compound as claimed in claim 1, which is N-methyl-N-cyclooctyl-3,4-methylenedioxybenzylamine-hydrochloride.

6. Pharmaceutical compositions in dosage unit form having sali-diuretic action, consisting essentially from about 5 to 500 mg of a compound as defined in claim 1 as the active substance.

7. Method of treating edemas and/or essentially hypertonia of human beings, which comprises administering an effective amount of a composition containing as the active ingredient a compound as defined in claim 1.

* * * * *